(12) United States Patent
Stapleton et al.

(10) Patent No.: US 11,241,307 B2
(45) Date of Patent: Feb. 8, 2022

(54) REPLACEMENT HEART VALVE WITH DIAPHRAGM

(71) Applicant: BOSTON SCIENTIFIC SCIMED, INC., Maple Grove, MN (US)

(72) Inventors: Fionn Stapleton, Galway (IE); Sean O'Sullivan, Galway (IE); John Kilcooley, Galway (IE); Niamh McNamara, Galway (IE); Desmond McGreevy, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 424 days.

(21) Appl. No.: 15/783,003

(22) Filed: Oct. 13, 2017

(65) Prior Publication Data

US 2018/0104057 A1 Apr. 19, 2018

Related U.S. Application Data

(60) Provisional application No. 62/407,630, filed on Oct. 13, 2016.

(51) Int. Cl.
*A61F 2/24* (2006.01)
*A61F 2/90* (2013.01)

(52) U.S. Cl.
CPC ............ *A61F 2/2421* (2013.01); *A61F 2/243* (2013.01); *A61F 2/2409* (2013.01); *A61F 2/2436* (2013.01); *A61F 2/90* (2013.01); *A61F 2220/0008* (2013.01); *A61F 2230/0006* (2013.01)

(58) Field of Classification Search
CPC ........ A61F 2/24; A61F 2/2409; A61F 2/2412; A61F 2/2418; A61F 2/2421; A61F 2/2475; A61F 2/243; A61F 2/2436; A61F 2/90; A61F 2220/0008; A61F 2230/0006
See application file for complete search history.

(56) References Cited

U.S. PATENT DOCUMENTS

| | | | |
|---|---|---|---|
| 3,370,305 A | 2/1968 | Goott et al. | |
| 3,374,489 A | 3/1968 | Alvarez Diaz | |
| 3,451,067 A | 6/1969 | Jordan | |

(Continued)

OTHER PUBLICATIONS

US 9,265,606, 02/2016, Buchbinder et al. (withdrawn)

(Continued)

*Primary Examiner* — Ryan J. Severson
(74) *Attorney, Agent, or Firm* — Seager, Tufte & Wickhem LLP (57) ABSTRACT

A replacement heart valve system may include a delivery sheath and a replacement heart valve. The replacement heart valve may include a mesh anchor member disposed within the delivery sheath in an elongated delivery configuration, the mesh anchor member being expandable to a deployed configuration when unconstrained by the delivery sheath. The mesh anchor member may include an upstream chamber, a downstream chamber, and a tubular middle portion extending between the upstream chamber and the downstream chamber. The replacement heart valve may include a diaphragm disposed within the downstream chamber of the mesh anchor member, wherein the diaphragm is configured to selectively prevent fluid flow through the replacement heart valve.

3 Claims, 8 Drawing Sheets

(56) References Cited

U.S. PATENT DOCUMENTS

| | | |
|---|---|---|
| 3,524,202 A | 8/1970 | Cromie |
| 3,534,411 A | 10/1970 | Shiley |
| 3,574,865 A | 4/1971 | Hamaker |
| 3,725,961 A | 4/1973 | Magovern et al. |
| 3,858,246 A | 1/1975 | Milo |
| 3,938,197 A | 2/1976 | Milo |
| 4,204,283 A | 5/1980 | Bellhouse et al. |
| 4,218,783 A | 8/1980 | Reul et al. |
| 4,225,980 A | 10/1980 | Ramos Martinez |
| 4,263,680 A | 4/1981 | Reul et al. |
| 4,340,977 A | 7/1982 | Brownlee et al. |
| 4,345,340 A | 8/1982 | Rosen |
| 4,490,859 A | 1/1985 | Black et al. |
| 4,680,031 A | 7/1987 | Alonso |
| 4,731,075 A | 3/1988 | Gallo Mezo et al. |
| 4,759,759 A | 7/1988 | Walker et al. |
| 5,332,402 A | 7/1994 | Teitelbaum |
| 5,405,382 A | 4/1995 | Kukolnikov et al. |
| 8,403,979 B2 | 3/2013 | Paul, Jr. |
| 8,926,691 B2 | 1/2015 | Chau et al. |
| 8,926,694 B2 | 1/2015 | Costello |
| 8,956,404 B2 | 2/2015 | Bortlein et al. |
| 8,986,373 B2 | 3/2015 | Chau et al. |
| 8,992,604 B2 | 3/2015 | Gross et al. |
| 9,011,515 B2 | 4/2015 | Schweich, Jr. et al. |
| 9,017,399 B2 | 4/2015 | Gross et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,066,800 B2 | 6/2015 | Clague et al. |
| 9,072,603 B2 | 7/2015 | Tuval et al. |
| 9,084,676 B2 | 7/2015 | Chau et al. |
| 9,095,433 B2 | 8/2015 | Lutter et al. |
| 9,119,713 B2 | 9/2015 | Board et al. |
| 9,125,740 B2 | 9/2015 | Morriss et al. |
| 9,155,617 B2 | 10/2015 | Carpentier et al. |
| 9,192,466 B2 | 11/2015 | Kovalsky et al. |
| 9,241,790 B2 | 1/2016 | Lane et al. |
| 9,248,014 B2 | 2/2016 | Lane et al. |
| 9,254,192 B2 | 2/2016 | Lutter et al. |
| 9,280,291 B2 | 3/2016 | Gorman, III et al. |
| 9,295,547 B2 | 3/2016 | Costello et al. |
| 9,295,552 B2 | 3/2016 | McLean et al. |
| 9,301,836 B2 | 4/2016 | Buchbinder et al. |
| 9,308,087 B2 | 4/2016 | Lane et al. |
| 9,326,850 B2 | 5/2016 | Venkatasubramanian |
| 9,333,073 B2 | 5/2016 | Quadri et al. |
| 9,333,074 B2 | 5/2016 | Quadri et al. |
| 9,339,377 B2 | 5/2016 | Quadri et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,381 B2 | 5/2016 | Johnson |
| 9,339,382 B2 | 5/2016 | Tabor et al. |
| 9,345,572 B2 | 5/2016 | Cerf et al. |
| 9,358,108 B2 | 6/2016 | Bortlein et al. |
| 9,387,078 B2 | 7/2016 | Gross et al. |
| 9,421,098 B2 | 8/2016 | Gifford, III et al. |
| 9,427,315 B2 | 8/2016 | Schweich, Jr. et al. |
| 9,427,316 B2 | 8/2016 | Schweich, Jr. et al. |
| 9,433,500 B2 | 9/2016 | Chau et al. |
| 2001/0021872 A1* | 9/2001 | Bailey ............... A61F 2/2418 623/1.24 |
| 2007/0142906 A1 | 6/2007 | Figulla et al. |
| 2008/0288055 A1* | 11/2008 | Paul, Jr. ............. A61F 2/2412 623/1.24 |
| 2012/0130468 A1* | 5/2012 | Khosravi ............ A61F 2/915 623/1.11 |
| 2014/0025164 A1 | 1/2014 | Montorfano et al. |
| 2014/0155992 A1 | 6/2014 | Palmaz |
| 2014/0257476 A1 | 9/2014 | Montorfano et al. |
| 2014/0350669 A1 | 11/2014 | Gillespie et al. |
| 2014/0358223 A1 | 12/2014 | Rafiee et al. |
| 2014/0358224 A1 | 12/2014 | Tegels et al. |
| 2014/0371844 A1 | 12/2014 | Dale et al. |
| 2014/0379076 A1 | 12/2014 | Vidlund et al. |
| 2015/0005875 A1 | 1/2015 | Tuval et al. |
| 2015/0025623 A1 | 1/2015 | Granada et al. |
| 2015/0039081 A1 | 2/2015 | Costello |
| 2015/0088248 A1 | 3/2015 | Scorsin et al. |
| 2015/0127096 A1 | 5/2015 | Rowe et al. |
| 2015/0142100 A1 | 5/2015 | Morriss et al. |
| 2015/0142103 A1 | 5/2015 | Vidlund |
| 2015/0150678 A1 | 6/2015 | Brecker |
| 2015/0157458 A1 | 6/2015 | Thambar et al. |
| 2015/0164640 A1 | 6/2015 | McLean et al. |
| 2015/0173897 A1 | 6/2015 | Raanani et al. |
| 2015/0173898 A1 | 6/2015 | Drasler et al. |
| 2015/0196390 A1 | 7/2015 | Ma et al. |
| 2015/0202044 A1 | 7/2015 | Chau et al. |
| 2015/0209139 A1 | 7/2015 | Granada et al. |
| 2015/0209143 A1 | 7/2015 | Duffy et al. |
| 2015/0216655 A1 | 8/2015 | Lane et al. |
| 2015/0216661 A1 | 8/2015 | Hacohen et al. |
| 2015/0238314 A1 | 8/2015 | Bortlein et al. |
| 2015/0257877 A1 | 9/2015 | Hernandez |
| 2015/0257878 A1 | 9/2015 | Lane et al. |
| 2015/0257879 A1 | 9/2015 | Bortlein et al. |
| 2015/0257881 A1 | 9/2015 | Bortlein et al. |
| 2015/0257882 A1 | 9/2015 | Bortlein et al. |
| 2015/0272737 A1 | 10/2015 | Dale et al. |
| 2015/0320553 A1 | 11/2015 | Chau et al. |
| 2015/0327994 A1 | 11/2015 | Morriss et al. |
| 2015/0327999 A1 | 11/2015 | Board et al. |
| 2015/0328000 A1 | 11/2015 | Ratz et al. |
| 2015/0328001 A1 | 11/2015 | McLean et al. |
| 2015/0328002 A1 | 11/2015 | McLean et al. |
| 2015/0335424 A1 | 11/2015 | McLean et al. |
| 2015/0335429 A1 | 11/2015 | Morriss et al. |
| 2015/0351903 A1 | 12/2015 | Morriss et al. |
| 2015/0351904 A1 | 12/2015 | Cooper et al. |
| 2015/0359629 A1 | 12/2015 | Ganesan et al. |
| 2015/0359631 A1 | 12/2015 | Sheahan et al. |
| 2016/0242905 A1 | 1/2016 | Johnson et al. |
| 2016/0242906 A1 | 1/2016 | Jamison et al. |
| 2016/0030171 A1 | 2/2016 | Quijano et al. |
| 2016/0038280 A1 | 2/2016 | Morriss et al. |
| 2016/0038283 A1 | 2/2016 | Divekar et al. |
| 2016/0051362 A1 | 2/2016 | Cooper et al. |
| 2016/0074160 A1 | 3/2016 | Christianson et al. |
| 2016/0089234 A1 | 3/2016 | Gifford, III |
| 2016/0089235 A1 | 3/2016 | Yellin |
| 2016/0089238 A1 | 3/2016 | Centola et al. |
| 2016/0095700 A1 | 4/2016 | Righini |
| 2016/0095701 A1 | 4/2016 | Dale et al. |
| 2016/0106539 A1 | 4/2016 | Buchbinder et al. |
| 2016/0113764 A1 | 4/2016 | Sheahan et al. |
| 2016/0113765 A1 | 4/2016 | Ganesan et al. |
| 2016/0113768 A1 | 4/2016 | Ganesan et al. |
| 2016/0120643 A1 | 5/2016 | Kupumbati |
| 2016/0143730 A1 | 5/2016 | Kheradvar |
| 2016/0151154 A1 | 6/2016 | Gorman, III et al. |
| 2016/0157999 A1 | 6/2016 | Lane et al. |
| 2016/0158000 A1 | 6/2016 | Granada et al. |
| 2016/0158002 A1 | 6/2016 | Wallace et al. |
| 2016/0158013 A1 | 6/2016 | Carpentier et al. |
| 2016/0184095 A1 | 6/2016 | Spence et al. |
| 2016/0206424 A1 | 7/2016 | Al-Jilaihaw et al. |
| 2016/0213469 A1 | 7/2016 | Shu et al. |
| 2016/0228248 A1 | 8/2016 | Rowe et al. |
| 2016/0235526 A1 | 8/2016 | Lashinski et al. |
| 2016/0235529 A1 | 8/2016 | Ma et al. |
| 2016/0242902 A1 | 8/2016 | Morriss et al. |

OTHER PUBLICATIONS

"A Technical Review of Minimally Invasive Mitral Valve Replacements"—Cardiovascular Engineering and Technology; Nov. 25, 2014.

(56) References Cited

OTHER PUBLICATIONS

International Search Report and Written Opinion dated Dec. 22, 2017 for International Application No. PCT/US2017/056537.

* cited by examiner

REPLACEMENT HEART VALVE WITH DIAPHRAGM

CROSS REFERENCE TO RELATED APPLICATIONS

The present application claims the benefit of and priority to U.S. Provisional Patent Application Ser. No. 62/407,630, filed Oct. 13, 2016, the disclosure of which is incorporated herein by reference

TECHNICAL FIELD

The present disclosure pertains to medical devices, and methods for manufacturing and/or using medical devices. More particularly, the present disclosure pertains to a replacement heart valve and/or apparatus and methods of manufacture therefor.

BACKGROUND

A wide variety of intracorporeal medical devices have been developed for medical use, for example, surgical and/or intravascular use. Some of these devices include guidewires, catheters, medical device delivery systems (e.g., for stents, grafts, replacement valves, etc.), and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and/or using medical devices.

SUMMARY

In a first aspect, a replacement heart valve configured for implantation within an annulus of a native heart valve may comprise an anchor member including an upstream portion forming an upstream chamber, a downstream portion forming a downstream chamber, and a tubular middle portion disposed between the upstream portion and the downstream portion, and a disc-shaped diaphragm disposed within the downstream chamber of the anchor member. The tubular middle portion forms a longitudinally-oriented lumen extending between the upstream portion and the downstream portion.

In addition or alternatively, and in a second aspect, the tubular middle portion is positionable within the annulus of the native heart valve with the upstream chamber disposed upstream of the annulus and the downstream chamber disposed downstream of the annulus.

In addition or alternatively, and in a third aspect, the disc-shaped diaphragm includes a fluid impermeable material disposed over a support ring.

In addition or alternatively, and in a fourth aspect, the support ring extends radially outward of the tubular middle portion.

In addition or alternatively, and in a fifth aspect, the fluid impermeable material extends radially outward of the tubular middle portion.

In addition or alternatively, and in a sixth aspect, the disc-shaped diaphragm is free to move axially within the downstream chamber of the anchor member in response to fluid flow through the tubular middle portion.

In addition or alternatively, and in a seventh aspect, the disc-shaped diaphragm moves away from the tubular middle portion, thereby permitting fluid flow through the tubular middle portion, in response to a positive fluid pressure differential between the tubular middle portion and the downstream portion.

In addition or alternatively, and in an eighth aspect, the disc-shaped diaphragm moves against the tubular middle portion, thereby preventing fluid flow through the tubular middle portion, in response to a negative fluid pressure differential between the tubular middle portion and the downstream portion.

In addition or alternatively, and in a ninth aspect, the upstream chamber extends radially outward from the tubular middle portion.

In addition or alternatively, and in a tenth aspect, the downstream chamber extends radially outward from the tubular middle portion.

In addition or alternatively, and in an eleventh aspect, the upstream portion of the anchor member includes a first upstream portion and a first downstream portion adjacent the tubular middle portion, the first downstream portion being spaced apart from the first upstream portion by a first circumferential portion. The first upstream portion, the first downstream portion, and the first circumferential portion collectively define the upstream chamber.

In addition or alternatively, and in a twelfth aspect, the downstream portion of the anchor member includes a second downstream portion and a second upstream portion adjacent the tubular middle portion, the second downstream portion being spaced apart from the second upstream portion by a second circumferential portion. The second upstream portion, the second downstream portion, and the second circumferential portion collectively define the downstream chamber.

In addition or alternatively, and in a thirteenth aspect, the anchor member includes a fluid impermeable coating contiguously disposed on a portion of the upstream chamber, a portion of the downstream chamber, and the tubular middle portion between the upstream chamber and the downstream chamber.

In addition or alternatively, and in a fourteenth aspect, the anchor member comprises a wire braid.

In addition or alternatively, and in a fifteenth aspect, a replacement heart valve system may comprise a delivery sheath and a replacement heart valve. The replacement heart valve may comprise a mesh anchor member disposed within the delivery sheath in an elongated delivery configuration, wherein the mesh anchor member includes an upstream chamber, a downstream chamber, and a tubular middle portion extending between the upstream chamber and the downstream chamber; and a diaphragm disposed within the downstream chamber of the mesh anchor member. The mesh anchor member is expandable to a deployed configuration when unconstrained by the delivery sheath. The diaphragm is configured to selectively prevent fluid flow through the replacement heart valve.

In addition or alternatively, and in a sixteenth aspect, the diaphragm is configured to move toward or away from the tubular middle portion within the downstream chamber. When the diaphragm is disposed in contact with the tubular middle portion, retrograde fluid flow through the replacement heart valve is prevented. When the diaphragm is spaced apart from the tubular middle portion, antegrade fluid flow through the replacement heart valve is permitted.

In addition or alternatively, and in a seventeenth aspect, a downstream end of the tubular middle portion is generally flush with the downstream chamber.

In addition or alternatively, and in an eighteenth aspect, a replacement heart valve configured for implantation within an annulus of a native heart valve may comprise a self-expanding wire mesh anchor member including an upstream portion forming a hollow upstream chamber, a downstream portion forming a hollow downstream chamber, and a generally cylindrical middle portion extending between the upstream portion and the downstream portion, wherein the middle portion forms a longitudinally-oriented lumen extending between the upstream portion and the downstream portion; a disc-shaped diaphragm disposed within the downstream chamber of the anchor member, wherein the diaphragm is configured to selectively permit and prevent fluid flow through the longitudinally-oriented lumen of the middle portion; and a fluid impermeable coating contiguously disposed on a portion of the upstream chamber, a portion of the downstream chamber, and the middle portion between the upstream chamber and the downstream chamber. An outer extent of the upstream portion is greater than a diameter of the middle portion, and an outer extent of the downstream portion is greater than the diameter of the middle portion.

In addition or alternatively, and in a nineteenth aspect, the diaphragm is configured to move toward or away from the middle portion within the downstream chamber in response to a direction of fluid flow through the replacement heart valve.

During systole, the diaphragm is disposed in contact with the middle portion and retrograde fluid flow through the longitudinally-oriented lumen of the middle portion is prevented. During diastole, the diaphragm is spaced apart from the middle portion and antegrade fluid flow through the longitudinally-oriented lumen of the middle portion is permitted.

In addition or alternatively, and in a twentieth aspect, the anchor member is configured to self-expand from an elongated delivery configuration to a radially-expanded and longitudinally-shortened deployed configuration when unconstrained. When the anchor member is positioned within a native heart valve in the deployed configuration, the anchor member is configured to sandwich valve leaflets of the native heart valve between the upstream portion and the downstream portion.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE DRAWINGS

The disclosure may be more completely understood in consideration of the following detailed description of various embodiments in connection with the accompanying drawings, in which.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed invention. Those skilled in the art will recognize that the various elements described and/or shown may be arranged in various combinations and configurations without departing from the scope of the disclosure. The detailed description and drawings illustrate example embodiments of the claimed invention.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosed invention are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

Diseases and/or medical conditions that impact the cardiovascular system are prevalent throughout the world. Traditionally, treatment of the cardiovascular system was often conducted by directly accessing the impacted part of the system. For example, treatment of a blockage in one or more of the coronary arteries was traditionally treated using coronary artery bypass surgery. As can be readily appreciated, such therapies are rather invasive to the patient and require significant recovery times and/or treatments. More recently, less invasive therapies have been developed, for example, where a blocked coronary artery could be accessed and treated via a percutaneous catheter (e.g., angioplasty). Such therapies have gained wide acceptance among patients and clinicians.

Figure 1:
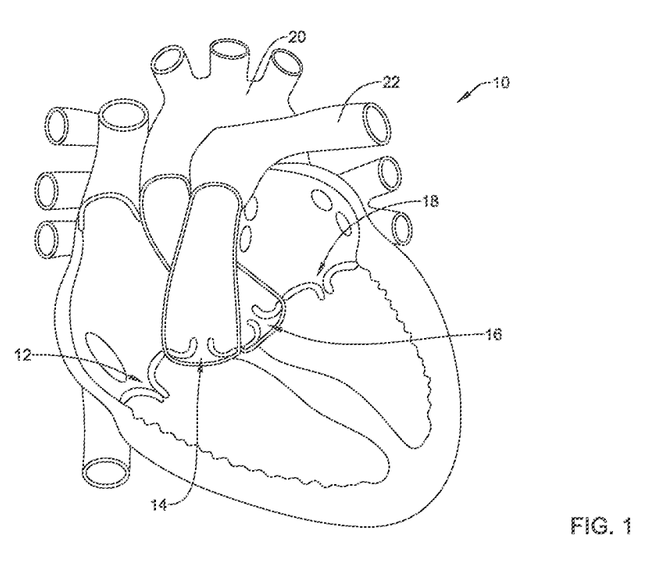
FIG. 1 is a partial cut-away view of an example heart.

Some mammalian hearts (e.g., human, etc.) include four heart valves: a tricuspid valve 12, a pulmonary valve 14, an aortic valve 16, and a mitral valve 18, as seen in an example heart 10 illustrated in FIG. 1. The purpose of the heart valves is to allow blood to flow through the heart 10 and from the heart 10 into the major blood vessels connected to the heart 10, such as the aorta 20 and the pulmonary artery 22, for example. In a normally functioning heart valve, blood is permitted to pass or flow downstream through the heart valve (e.g., from an atrium to a ventricle, from a ventricle to an artery, etc.) when the heart valve is open, and when the heart valve is closed, blood is prevented from passing or flowing back upstream through the heart valve (e.g., from a ventricle to an atrium, etc.). Some relatively common medical conditions may include or be the result of inefficiency, ineffectiveness, or complete failure of one or more of the valves within the heart. Treatment of defective heart valves poses other challenges in that the treatment often requires the repair or outright replacement of the defective valve. Such therapies may be highly invasive to the patient. Disclosed herein are medical devices that may be used within a portion of the cardiovascular system in order to diagnose, treat, and/or repair the system. At least some of the medical devices disclosed herein may include a replacement heart valve (e.g., a replacement aortic valve, a replacement mitral valve, etc.) and may reduce, treat, and/or prevent the occurrence of defects such as (but not limited to) regurgitation, leaflet prolapse, and/or valve stenosis. In addition, the devices disclosed herein may deliver the replacement heart valve percutaneously and, thus, may be much less invasive to the patient, although other surgical methods and approaches may also be used. The devices disclosed herein may also provide a number of additional desirable features and benefits as described in more detail below. For the purpose of this disclosure, the discussion below is directed toward a replacement mitral valve and will be so described in the interest of brevity. This, however, is not intended to be limiting as the skilled person will recognize that the following discussion may also apply to a replacement aortic valve or another replacement heart valve with no or minimal changes to the structure and/or scope of the disclosure.

Figure 2:
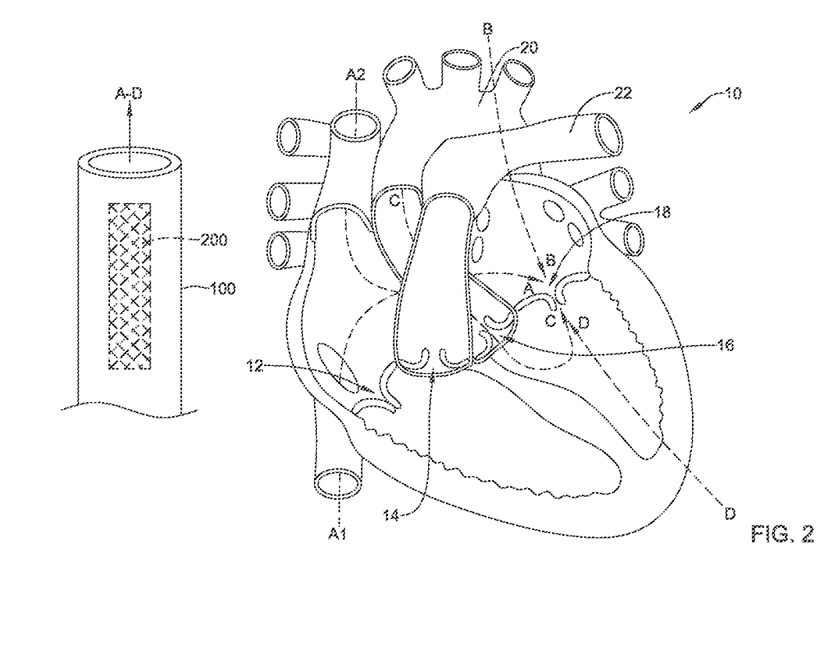
FIG. 2 illustrates several possible approaches for delivery of a replacement heart valve.

An example replacement heart valve system may include a delivery sheath 100, such as those known and/or used with replacement heart valves, and a replacement heart valve 200 configured for implantation within an annulus of a native heart valve. The replacement heart valve 200 may include an anchor member 210 disposed within a lumen of the delivery sheath 100 proximate a distal end of the delivery sheath 100 in an elongated delivery configuration, as seen in FIG. 2 for example, the anchor member 210 being expandable to a deployed configuration when unconstrained by the delivery sheath 100. Further details regarding the replacement heart valve 200 will be described below. FIG. 2 illustrates several possible approaches that may be used to deliver the replacement heart valve 200 to the mitral valve 18 with the delivery sheath 100.

In some embodiments, the replacement heart valve 200 may be delivered percutaneously to the mitral valve 18 via a transseptal approach "A". Within the transseptal approach "A", which involves transiting the septum of the heart 10, the delivery sheath 100 may be advanced into right atrium of the heart 10 through the inferior vena cava ("A1") or the superior vena cava ("A2") before transiting the septum. In some embodiments, the replacement heart valve 200 may be delivered surgically to the mitral valve 18 via a left atriotomy "B", which involves surgically opening the left atrium of the heart 10. In some embodiments, the replacement heart valve 200 may be delivered percutaneously to the mitral valve 18 via a transaortic approach "C", which involves transiting the aorta 20 (from a femoral entry point in some cases), the aortic arch, the aortic valve 16, and the left ventricle of the heart 10. In some embodiments, the replacement heart valve 200 may be delivered surgically to the mitral valve 18 via a transapical approach "D". Within the transapical approach "D", which involves transiting the wall of the left ventricle of the heart 10. Certain constructional details of the delivery sheath 100 (e.g., length, stiffness, column strength, etc.) may be adjusted according to the approach used in any given procedure. Some suitable but non-limiting materials for the delivery sheath 100, for example metallic materials, polymer materials, composite materials, etc., are described below.

Figure 3:
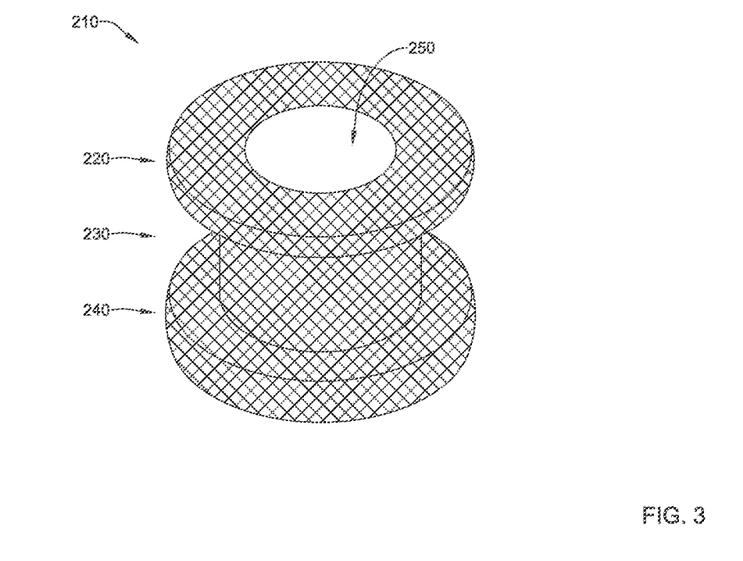
FIG. 3 illustrates an example anchor member of an example replacement heart valve.

FIG. 3 illustrates an example anchor member 210 in the deployed configuration. In some embodiments, the anchor member 210 may include and/or be formed as a wire mesh or braid, a stent-like structure, or other suitable expandable configuration. In some embodiments, the anchor member 210 may be formed as a self-expanding wire mesh or braid, although assisted expansion is also contemplated. In at least some embodiments, the anchor member 210 may be formed as a unitary structure (e.g., formed from a single filament or strand of wire, cut from a single tubular member, etc.). Other configurations, including the anchor member 210 being formed from a plurality of interwoven filaments or wires, are also contemplated. In some embodiments, the anchor member 210 may be configured to expand and/or self-expand from an elongated delivery configuration to a radially-expanded and/or longitudinally-shortened deployed configuration when unconstrained (e.g., after being released from the delivery sheath 100, etc.).

In some embodiments, the anchor member 210 may include an upstream portion forming a hollow upstream chamber 220, a downstream portion forming a hollow downstream chamber 240, and a tubular and/or generally cylindrical middle portion 230 disposed and/or extending between the upstream portion and/or the upstream chamber 220 and the downstream portion and/or the downstream chamber 240. The middle portion 230 forms a longitudinally-oriented lumen 250 extending between the upstream portion and/or the upstream chamber 220 and the downstream portion and/or the downstream chamber 240, and/or extending through the anchor member 210 of the replacement heart valve 200. In the delivery configuration, the upstream portion may extend axially from the middle portion 230, and/or be generally aligned with and/or oriented parallel to the middle portion 230. The upstream portion and/or the upstream chamber 220 extends radially outward from the middle portion 230 in the deployed configuration. In other words, an outer diameter or an outer extent of the upstream portion and/or the upstream chamber 220 is greater than an outer diameter or an outer extent of the middle portion 230 in the deployed configuration. In the delivery configuration, the downstream portion may extend axially from the middle portion 230, and/or be generally aligned with and/or oriented parallel to the middle portion 230. The downstream portion and/or the downstream chamber 240 extends radially outward from the middle portion 230 in the deployed configuration. In other words, an outer diameter or an outer extent of the downstream portion and/or the downstream chamber 240 is greater than an outer diameter or an outer extent of the middle portion 230 in the deployed configuration.

Figure 4:
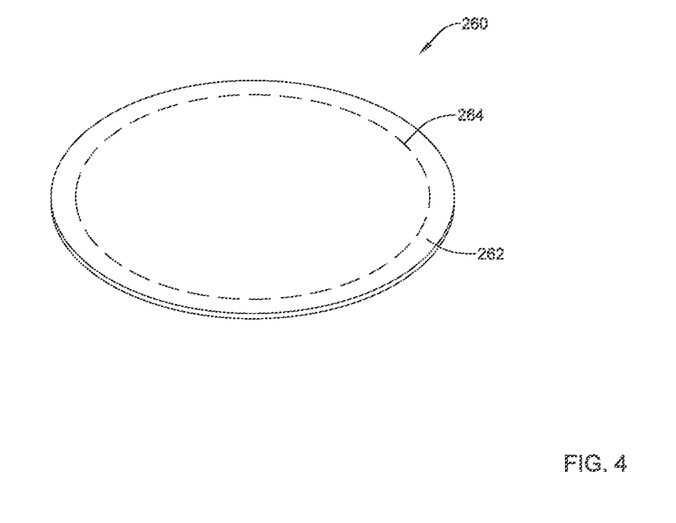
FIG. 4 illustrates an example diaphragm of an example replacement heart valve.

The replacement heart valve 200 may include a disc-shaped diaphragm 260 configured to selectively permit and/or prevent fluid flow through the replacement heart valve 200 and/or through the longitudinally-oriented lumen 250 of the middle portion 230. FIG. 4 illustrates an example diaphragm 260. In general, the diaphragm 260 may have a flattened disc-like shape. In at least some embodiments, the diaphragm may include and/or be formed from a fluid impermeable material 262 disposed over a support ring 264. The fluid impermeable material 262 may extend radially outward of the support ring 264. In at least some embodiments, the support ring 264 may be encapsulated in the fluid impermeable material 262. In some embodiments, the diaphragm 260 may include reinforcement elements disposed within and/or on the fluid impermeable material 262, the reinforcement elements being configured to strengthen, stiffen, and/or support the fluid impermeable material 262. The reinforcement elements may be randomly oriented, radially oriented, axially oriented, or arranged in another suitable orientation as desired.

Figure 5:
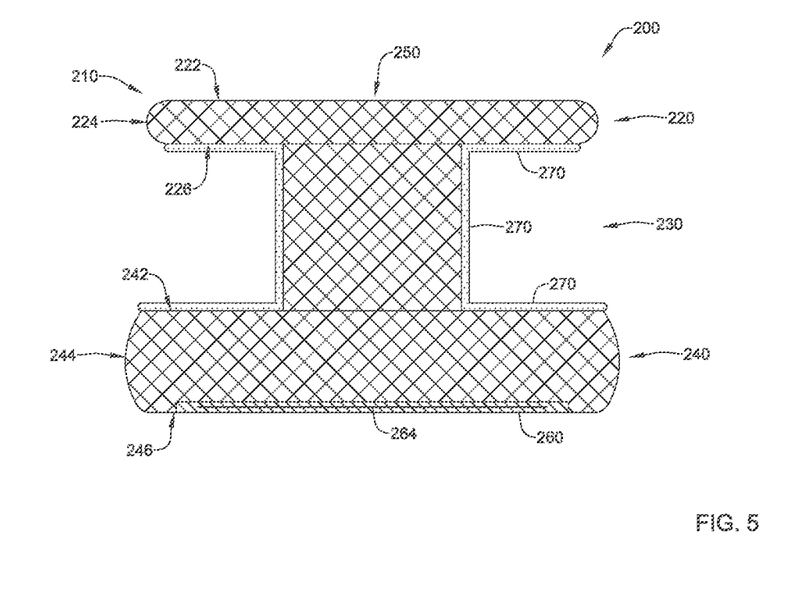
FIGS. 5-6 illustrate a cross-sectional view of an example replacement heart valve.
Figure 6:
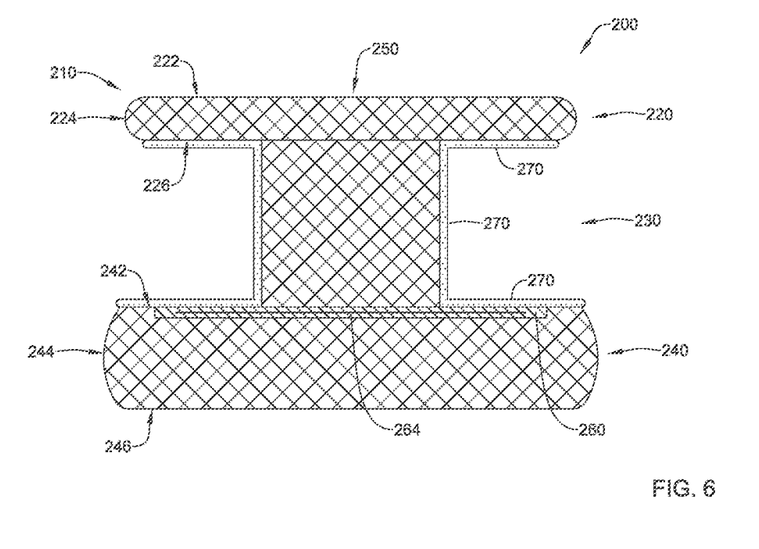

As shown in FIGS. 5 and 6, the upstream portion of the anchor member 210 may include a first upstream portion 222 and a first downstream portion 226 adjacent the middle portion 230 of the anchor member 210. The first upstream portion 222 may be spaced apart from the first downstream portion 226 by a first circumferential portion 224. The first upstream portion 222, the first downstream portion 226, and the first circumferential portion 224 may collectively define the upstream chamber 220. The downstream portion of the anchor member 210 may include a second downstream portion 246 and a second upstream portion 242 adjacent the middle portion 230 of the anchor member 210. The second downstream portion 246 may be spaced apart from the second upstream portion 242 by a second circumferential portion 244. The second upstream portion 242, the second downstream portion 246, and the second circumferential portion 244 may collectively define the downstream chamber 240. In some embodiments, an upstream end of the middle portion 230 may be generally flush with the upstream portion and/or the first downstream portion 226 of the upstream portion of the anchor member 210. A downstream end of the middle portion 230 may be generally flush with the downstream portion and/or the second upstream portion 242 of the downstream portion of the anchor member 210.

The anchor member 210 may include a fluid impermeable coating 270 disposed on and/or against at least a portion of an outer surface of the anchor member 210. In some embodiments, the fluid impermeable coating 270 may encapsulate and/or surround at least a portion of the wire mesh or braid, the stent-like structure, etc. of the anchor member 210 such that any gaps or openings that may be in fluid communication with the upstream chamber 220, the longitudinally-oriented lumen 250 of the middle portion 230, and/or the downstream chamber 240 are closed and/or sealed to fluid passage. In some embodiments, the fluid impermeable coating 270 may be contiguously disposed on and/or against at least a portion of the upstream portion and/or the upstream chamber 220 (e.g., the first downstream portion 226), on and/or against at least a portion of the downstream portion and/or the downstream chamber 240 (e.g., the second upstream portion 242), and on and/or against at least a portion of the middle portion 230 between the upstream portion and/or the upstream chamber 220 and the downstream portion and/or the downstream chamber 240. The fluid impermeable coating 270 may be configured to engage with and/or seal against the annulus and/or the leaflets of the native heart valve. In some embodiments, the fluid impermeable coating 270 may facilitate and/or encourage tissue ingrowth.

The diaphragm 260 may be disposed within the downstream chamber 240 of the anchor member 210. The support ring 264 of the diaphragm 260 may extend radially outward of the middle portion 230. The fluid impermeable material 262 of the diaphragm 260 may extend radially outward of the middle portion 230. In at least some embodiments, the diaphragm 260 may be configured and/or free to move axially within the downstream chamber 240 of the anchor member 210 in response to fluid flow through the middle portion 230 and/or the replacement heart valve 200. In other words, the diaphragm 260 may be configured to move toward or away from the downstream end of the middle portion 230 within the downstream chamber 240 in response to a direction of fluid flow through the middle portion 230 and/or the replacement heart valve 200.

In addition or alternatively, the diaphragm 260 may be configured to move toward or away from the downstream end of the middle portion 230 in response to a fluid pressure differential between the middle portion 230 and the downstream portion and/or the downstream chamber 240. For example, the diaphragm 260 may move away from the downstream end of the middle portion 230, as shown in FIG. 5 for example, thereby permitting fluid flow through the middle portion 230, in response to a positive fluid pressure differential between the middle portion 230 and the downstream portion and/or the downstream chamber 240 (e.g., fluid pressure is higher in the middle portion 230 than in the downstream portion and/or the downstream chamber 240). When the diaphragm 260 is spaced apart from the downstream end of the middle portion 230, antegrade fluid flow through the longitudinally-oriented lumen 250 of the middle portion 230 and/or the replacement valve 200 is permitted.

Similarly, the diaphragm 260 may move toward and/or against the downstream end of the middle portion 230, as shown in FIG. 6 for example, thereby preventing fluid flow through the middle portion 230, in response to a negative fluid pressure differential between the middle portion 230 and the downstream portion and/or the downstream chamber 240 (e.g., fluid pressure is lower in the middle portion 230 than in the downstream portion and/or the downstream chamber 240). When the diaphragm 260 is disposed in contact with the downstream end of the middle portion 230 and/or the second upstream portion 242 of the downstream portion of the anchor member 210, retrograde fluid flow through the longitudinally-oriented lumen 250 of the middle portion 230 and/or the replacement valve 200 is prevented.

Figure 7:
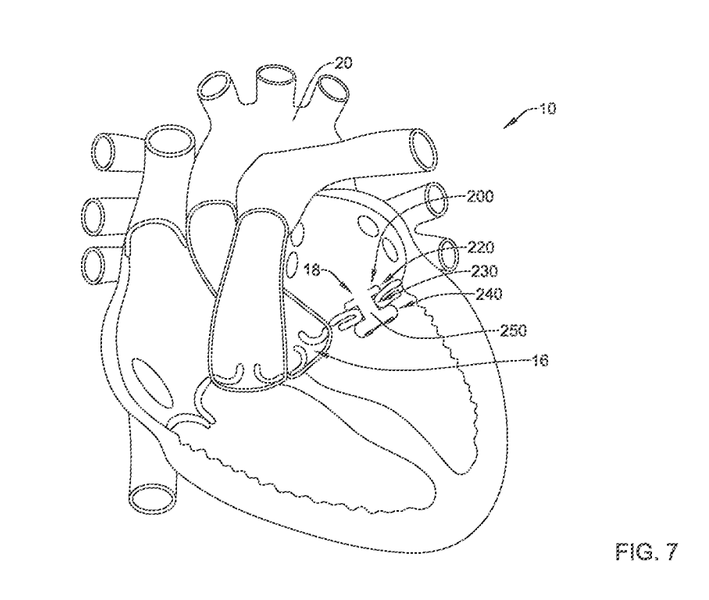
FIGS. 7-8 illustrate an example replacement heart valve in one example usage.
Figure 8:
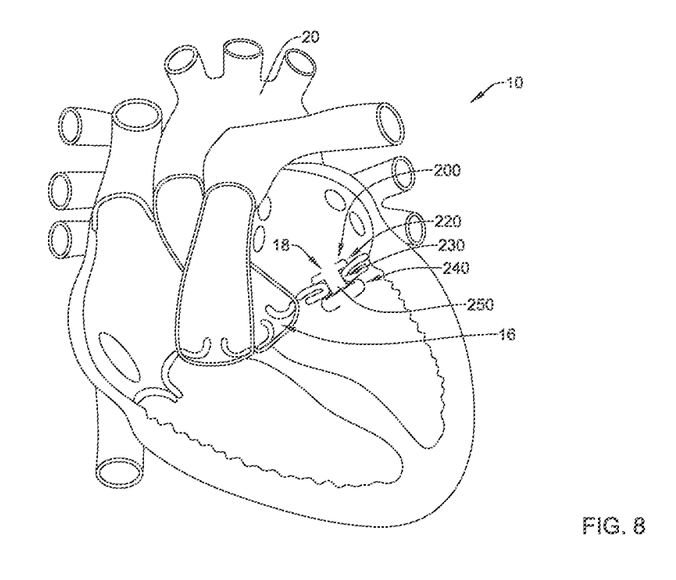

As discussed previously, the replacement heart valve 200 of the disclosure is generally described with respect to the use of the replacement heart valve 200 within and/or with respect to the native mitral valve 18 of the heart 10 (e.g., FIG. 1). In some embodiments, the replacement heart valve 200 and/or the anchor member 210 thereof may be released, deployed, and/or positioned within the annulus of a native heart valve, such as the mitral valve 18 as shown in FIGS. 7 and 8. The middle portion 230 may be positionable within the annulus of the native heart valve (e.g., mitral valve 18, etc.) with the upstream portion and/or the upstream chamber 220 disposed upstream of the annulus of the native heart valve (e.g., mitral valve 18, etc.) and the downstream portion and/or the downstream chamber 240 disposed downstream of the annulus of the native heart valve (e.g., mitral valve 18, etc.). In some embodiments, when the replacement heart valve 200 and/or the anchor member 210 is positioned within the annulus of the native heart valve (e.g., mitral valve 18, etc.) in the deployed configuration, the anchor member 210 may be configured to sandwich, to compress, and/or to hold in compression valve leaflets of the native heart valve (e.g., mitral valve 18, etc.) between the upstream portion and/or the upstream chamber 220 and the downstream portion and/or the downstream chamber 240. Such an arrangement, in addition to securely holding the replacement valve 200 in place, may reduce and/or limit the amount of radial force exerted on the annulus of the native heart valve (e.g., mitral valve 18, etc.) by the anchor member 210 and/or elements or portions thereof (e.g., the upstream portion, the middle portion, the downstream portion, etc.) and/or an adjacent native heart valve (for example, if positioned in the mitral valve 18 radial force exerted on the aortic valve 16 and/or the annulus thereof may be reduced and/or limited, etc.).

In other words, when positioned in the annulus of the mitral valve 18, the upstream portion and/or the upstream chamber 220 may be disposed in the left atrium of the heart 10, while the downstream portion and/or the downstream chamber 240 may be disposed in the left ventricle of the heart 10. Alternatively, when positioned in the annulus of the aortic valve 16, the upstream portion and/or the upstream chamber 220 may be disposed in the left ventricle of the heart 10, while the downstream portion and/or the downstream chamber 240 may be disposed in the aorta 20 and/or the aortic arch of the heart 10. Other configurations and use in other heart valves are also contemplated.

Following release, deployment, and/or positioning of the replacement heart valve 200 and/or the anchor member 210 within the annulus of the native heart valve (e.g., mitral valve 18, etc.), the diaphragm may be configured and/or free to move axially toward or away from the middle portion 230 of the anchor member 210 within the downstream chamber 240 in response to fluid flow through the longitudinally-oriented lumen 250 of the middle portion 230 and/or the replacement heart valve 200. Fluid flow through the longitudinally-oriented lumen 250 of the middle portion 230 and/or the replacement heart valve 200 may be a result of normal function of the heart 10 and/or fluid pressure differential between the middle portion 230 and the downstream portion and/or the downstream chamber 240 (e.g., across the native heart valve, across the replacement heart valve 200, across the annulus of the native heart valve, etc.). In other words, during systole, the diaphragm 260 may be disposed in and/or pushed into contact with the middle portion 230 and/or the second upstream portion 242 and retrograde fluid flow through the longitudinally-oriented lumen 250 of the middle portion 230 is prevented. During diastole, the diaphragm 260 may be disposed spaced apart from the middle portion 230 and/or the second upstream portion 242 and retrograde fluid flow through the longitudinally-oriented lumen 250 of the middle portion 230 is permitted.

The materials that can be used for the various components of the replacement heart valve system, the delivery sheath 100, the replacement heart valve 200, the anchor member 210, the diaphragm 260, etc. (and/or other systems or components disclosed herein) and the various elements thereof disclosed herein may include those commonly associated with medical devices. For simplicity purposes, the following discussion makes reference to the replacement heart valve system, the delivery sheath 100, the replacement heart valve 200, the anchor member 210, the diaphragm 260, etc. However, this is not intended to limit the devices and methods described herein, as the discussion may be applied to other elements, members, components, or devices disclosed herein, such as, but not limited to, the replacement heart valve system, the delivery sheath 100, the replacement heart valve 200, the anchor member 210, the diaphragm 260, etc. and/or elements or components thereof.

In some embodiments, the replacement heart valve system, the delivery sheath 100, the replacement heart valve 200, the anchor member 210, the diaphragm 260, etc., and/or components thereof (such as, but not limited to, the upstream portion, the middle portion 230, the downstream portion, the fluid impermeable material 262, the support ring 264, the fluid impermeable coating 270, etc.), may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the replacement heart valve system, the delivery sheath 100, the replacement heart valve 200, the anchor member 210, the diaphragm 260, etc., and/or components thereof, may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the replacement heart valve system, the delivery sheath 100, the replacement heart valve 200, the anchor member 210, the diaphragm 260, etc. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the replacement heart valve system, the delivery sheath 100, the replacement heart valve 200, the anchor member 210, the diaphragm 260, etc. to achieve the same result.

In some embodiments, a degree of Magnetic Resonance Imaging (MRI) compatibility is imparted into the replacement heart valve system, the delivery sheath 100, the replacement heart valve 200, the anchor member 210, the diaphragm 260, etc. For example, the replacement heart valve system, the delivery sheath 100, the replacement heart valve 200, the anchor member 210, the diaphragm 260, etc., and/or components or portions thereof, may be made of a material that does not substantially distort the image and create substantial artifacts (e.g., gaps in the image). Certain ferromagnetic materials, for example, may not be suitable because they may create artifacts in an MRI image. The replacement heart valve system, the delivery sheath 100, the replacement heart valve 200, the anchor member 210, the diaphragm 260, etc., or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the replacement heart valve system, the delivery sheath 100, the replacement heart valve 200, the anchor member 210, the diaphragm 260, etc., and/or portions thereof, may be made from or include a polymer or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

It should be understood that this disclosure is, in many respects, only illustrative. Changes may be made in details, particularly in matters of shape, size, and arrangement of steps without exceeding the scope of the invention. This may include, to the extent that it is appropriate, the use of any of the features of one example embodiment being used in other embodiments. The invention's scope is, of course, defined in the language in which the appended claims are expressed.

What is claimed is:

1. A replacement heart valve configured for implantation within an annulus of a native heart valve, comprising:
    a self-expanding wire mesh anchor member including an upstream portion forming a hollow upstream chamber, a downstream portion forming a hollow downstream chamber, and a generally cylindrical middle portion extending between the upstream portion and the downstream portion;
    wherein the generally cylindrical middle portion forms a longitudinally-oriented lumen extending between the upstream portion and the downstream portion;
    wherein an outer extent of the upstream portion is everywhere greater than a diameter of the generally cylindrical middle portion, and an outer extent of the downstream portion is everywhere greater than the diameter of the generally cylindrical middle portion;
    a disc-shaped diaphragm that includes a fluid impermeable material disposed over a circular support ring disposed within the hollow downstream chamber of the anchor member, wherein the disc-shaped diaphragm is configured to move axially to selectively permit and prevent fluid flow through the longitudinally-oriented lumen of the generally cylindrical middle portion; and
    a fluid impermeable coating contiguously disposed on a portion of the upstream chamber, a portion of the hollow downstream chamber, and the generally cylindrical middle portion between the upstream chamber and the hollow downstream chamber.

2. The replacement heart valve of claim 1, wherein the disc-shaped diaphragm is configured to move toward or away from the middle portion within the hollow downstream chamber in response to a direction of fluid flow through the replacement heart valve;
    wherein during systole, the disc-shaped diaphragm is disposed in contact with the middle portion and retrograde fluid flow through the longitudinally-oriented lumen of the middle portion is prevented; and
    wherein during diastole, the disc-shaped diaphragm is spaced apart from the middle portion and antegrade fluid flow through the longitudinally-oriented lumen of the middle portion is permitted.

3. The replacement heart valve of claim 2, wherein the anchor member is configured to self-expand from an elongated delivery configuration to a radially-expanded and longitudinally-shortened deployed configuration when unconstrained;
    wherein when the anchor member is positioned within a native heart valve in the deployed configuration, the anchor member is configured to sandwich valve leaflets of the native heart valve between the upstream portion and the downstream portion.

* * * * *